(12) United States Patent
Nuriya et al.

(10) Patent No.: US 9,709,555 B2
(45) Date of Patent: Jul. 18, 2017

(54) COMPOUND FOR GENERATING SECOND HARMONIC OF LIGHT, DYE COMPOSITION FOR GENERATING SECOND HARMONIC OF LIGHT, AND CELL EXAMINATION METHOD

(71) Applicants: KEIO UNIVERSITY, Minato-ku, Tokyo (JP); University of Tsukuba, Tsukuba-shi, Ibaraki (JP)

(72) Inventors: Mutsuo Nuriya, Tokyo (JP); Masato Yasui, Tokyo (JP); Tatsuo Arai, Tsukuba (JP); Atsuya Momotake, Tsukuba (JP); Syun Fukushima, Tsukuba (JP)

(73) Assignee: KEIO UNIVERSITY, Minato-Ku, Tokyo (JP)

(*) Notice: Subject to any disclaimer, the term of this patent is extended or adjusted under 35 U.S.C. 154(b) by 0 days.

(21) Appl. No.: 14/892,464

(22) PCT Filed: May 23, 2014

(86) PCT No.: PCT/JP2014/063754
§ 371 (c)(1),
(2) Date: Nov. 19, 2015

(87) PCT Pub. No.: WO2014/189145
PCT Pub. Date: Nov. 27, 2014

(65) Prior Publication Data
US 2016/0116460 A1    Apr. 28, 2016

(30) Foreign Application Priority Data
May 23, 2013  (JP) .................. 2013-109179

(51) Int. Cl.
| | | |
|---|---|---|
| G01N 33/50 | (2006.01) | |
| G01N 21/63 | (2006.01) | |
| C09B 29/036 | (2006.01) | |
| C09B 29/08 | (2006.01) | |
| C09B 44/12 | (2006.01) | |
| C09B 29/42 | (2006.01) | |

(52) U.S. Cl.
CPC ..... *G01N 33/5091* (2013.01); *C09B 29/0048* (2013.01); *C09B 29/081* (2013.01); *C09B 29/0803* (2013.01); *C09B 29/0805* (2013.01); *C09B 29/3639* (2013.01); *C09B 44/126* (2013.01); *G01N 21/636* (2013.01)

(58) Field of Classification Search
CPC ................................................. C09B 29/0048
See application file for complete search history.

(56) References Cited

U.S. PATENT DOCUMENTS 5,047,516 A   9/1991  Allen et al.
6,107,066 A   8/2000  Tsien et al.

FOREIGN PATENT DOCUMENTS

| EP | 0292139 A1 | 11/1988 |
|---|---|---|
| EP | 1153598 A2 | 5/2001 |
| JP | S6470452 A | 3/1989 |
| JP | H08122326 A | 5/1996 |
| JP | H09005243 A | 1/1997 |
| JP | H11508355 A | 7/1999 |
| JP | 2001316231 A | 11/2001 |
| JP | 2004212132 A | 7/2004 |
| JP | 2005029726 A | 2/2005 |
| JP | 2012014066 A | 1/2012 |
| JP | 2012137549 A | 7/2012 |
| WO | 2010034623 A1 | 4/2010 |

OTHER PUBLICATIONS

Dai Imaizumi et al: "Optical Second Harmonic Generation and Relaxation Dynamics of Aligned Azo-Dyes in Sol-Gel Derived Organic-Inorganic Film", Journal of Sol-Gel Science and Technology, Kluwer Academic Publishers, BO, vol. 19, No. 1-3, Dec. 1, 2000, pp. 383-386, XP019212670.
Extended European Search Report for European Patent Application No. 14801474.9; Dated: Nov. 15, 2016.
Katz H.E. et al: "Chromophore Structure, Second Harmonic Generation, and Orientational Order in Zirconium Phosphonate/Phosphate Self-Assembled Multilayers", Journal of the American Chemical Society, American Chemical Society, US, vol. 116, No. 15, Jan. 1, 1994, pp. 6636-6640, XP002361204.
Gao, L.H. et al., Second-Order Nonlinear Optical Langmuir-Blodgett Films Based on a Series of Azo Rare-Earth Coordination Compounds, Chemistry of Materials, 1995, vol. 7, No. 6, p. 1047-1049.
International Search Report corresponding to Application No. PCT/2013/063754; Date of Mailing: Aug. 19, 2014, with English translation.
Mutsuo Nuriya, "Imaging Membrane Potential Dynamics in Neurons", The Review of Laser Engineering, 2012, vol. 40, No. 4, pp. 224-229.

*Primary Examiner* — Bin Shen
(74) *Attorney, Agent, or Firm* — Cantor Colburn LLP (57) ABSTRACT

Provided are a compound that generates an SHG signal but has suppressed generation of a TPF signal. Also provided is a cell examination method using the same. A compound for generating a second harmonic of light, the compound being an azobenzene derivative of formula (1), or a salt thereof. (R1 and R2 independently represent alkyl groups having 6-12 carbon atoms, and R3 to R18 independently represent substituents selected from hydrogen, halogens, alkyl groups, alkoxy groups, aryl groups, amino groups, hydroxyl groups, nitro groups, and cyano groups, but R5 and R6, R9 and R10, R13 and R14, and R17 and R18 may combine together and form a ring structure having 5-7 carbon atoms. X represents —N+R19R20R21, a sulfonyl group, a carboxyl group, or an —OR group. Here, R19, R20, and R21 independently represent straight-chain or branched alkyl groups having 1-5 carbon atoms, and —OR represents a monovalent polyalkylene oxide group terminated by an alkoxy group. a is 0 or 1, b is 0 or 1, and n is an integer of 1-10.)

7 Claims, 4 Drawing Sheets

COMPOUND FOR GENERATING SECOND HARMONIC OF LIGHT, DYE COMPOSITION FOR GENERATING SECOND HARMONIC OF LIGHT, AND CELL EXAMINATION METHOD

This is the U.S. national stage of application No. PCT/JP2014/063754 filed on May 23, 2014. Priority under 35 U.S.C. §119(a) and 35 U.S.C. §365(b) is claimed from Japanese Application No. 2013-109179, filed May 23, 2013, the disclosure of which is also incorporated herein by reference.

TECHNICAL FIELD

The present invention relates to a novel compound for generating a second harmonic of light, a dye composition for generating a second harmonic of light and a cell examination method using the same.

BACKGROUND ART

In order to understand brain functions, it is first necessary to observe its physiological functions. Information processing of nerve cells that support the higher functions of the brain is conducted by a change in electrical potential in a cell membrane and, therefore, since development of the patch clamp technique, the measurement of the electrical potential in a cell membrane has been mainly carried out using the electrophysiological technique.

Brain tissues are formed by a network in which a large number of nerve cells and glial cells are combined in a complex way and each cell also has a very complicated structure, and observation by an electrophysiological technique was therefore restricted. For example, since many of spines that are considered to be crucial for information processing and fine dendrites that support the spines have very fine structures with a diameter of less than 1 micron, the size of a glass electrode becomes a problem for the spines and dendrites and they are not suitable for observation by the above described electrophysiological technique.

Therefore, the measurement and visualization of electrical potential in a membrane using an optical technique have been tried in place of an electrophysiological technique (Patent Documents 1 to 5). Many imaging procedures on the basis of observation of fluorescence from electrical potential sensitive dyes and green fluorescent proteins (GFP) have been developed so far; however, have two large problems regarding time resolution ability and quantitativity. The utilization of second harmonic generation (SHG) imaging has been proposed as a technique capable of overcoming these problems, (Patent Documents 4 and 5).

SHG is a two-photon phenomenon in which two photons interact with a non-centrosymmetric substance and then transferred to the same direction as the incident angle as one photon having doubled energy. Observation utilizing SHG can use high-tissue-permeability near-infrared light from a two-photon microscope and thus it is suitable for observation of a deep part of a tissue. In observation utilizing a fluorescent dye, the dye absorbs one or two photons to be excited and, after relaxation, returns to the ground state, a quantitative measurement is fundamentally impossible; on the contrary, quantitative visualizations of membrane electrical potential that do not depend on cell form can be possible using this SHG imaging. In addition, the capability of preventing damage to a living tissue, which is caused by excitation of a dye, is also one of advantages.

When FM4-64, which is a known florescent dye, is introduced into a nerve cell from the cell exterior and irradiated with a femtosecond laser, a very strong SHG signal is detected by a detector in a light transmitted path in addition to a fluorescent (TPF) signal (Patent Document 4). Employment of this method enabled observation of fine structures such as distal dendrites and spines. Furthermore, it was also confirmed that when membrane electrical potential in a cell is changed by a membrane electrical potential fixing method, a SHG signal is accordingly reliably changed.

Patent Document 1: Japanese Unexamined Patent Application, Publication No. H08-122326
Patent Document 2: Japanese Unexamined Patent Application, Publication No. H09-005243
Patent Document 3: Japanese Unexamined Patent Application (Translation of PCT Application), Publication No. H11-508355
Patent Document 4: Japanese Unexamined Patent Application, Publication No. 2004-212132
Patent Document 5: Japanese Unexamined Patent Application, Publication No. 2012-14066

DISCLOSURE OF THE INVENTION

Problems to be Solved by the Invention

Currently, the above described dye using the FM4-64 is the most general dye capable of application in SHG imaging, but this dye is developed for fluorescence, so, apart from the SHG signal, fluorescence is also simultaneously generated, which results in the problem of damaging living tissue. Therefore, a compound that generates a SHG signal but has a TPF signal suppressed to be weak or does not generate a TPF signal has been desired for observation.

The present invention is made in view of the above described circumstances, and an object is to provide a compound that effectively acts on a cell membrane, generates an SHG signal but has suppressed generation of a TPF signal, and a cell examination method using the compound.

Means for Solving the Problems

The present inventors found that a compound having a specific chemical structure effectively acts on a cell membrane, generates an SHG signal but has suppressed generation of a TPF signal, and achieved completion of the present invention.

The first aspect of the present invention is a compound for generating a second harmonic of light, which is an azobenzene derivative expressed by the following formula (1) or a salt thereof:

(1)

(wherein each of R1 and R2 independently represents a straight-chain or branched alkyl group having 6 to 12 carbon atoms, and each of R3 to R18 independently represents a substituent selected from hydrogen, halogen, an alkyl group, an alkoxy group, an aryl group, an amino group, a hydroxyl group, a nitro group and a cyano group, R5 and R6, R9 and R10, R13 and R14, and R17 and R18 may combine together and form a ring structure having 5 to 7 carbon atoms. X represents —N+R19R20R21, a sulfonyl group, a carboxyl group, or an —OR group. Here, each of R19, R20 and R21 independently represents a straight-chain or branched alkyl group having 1 to 5 carbon atoms, and —OR represents a monovalent polyalkylene oxide group having an alkoxy group in the end. Provided that a is 0 or 1, b is 0 or 1, and n is an integer from 1 to 10.)

The second aspect of the present invention is a dye composition for generating a second harmonic of light containing the compound according to the first aspect.

The third aspect of the present invention is a cell examination method utilizing a second harmonic generated by the compound for generating a second harmonic of light of the first aspect around a cell membrane, which includes a dye introduction step of introducing the dye composition for generating a second harmonic of light according to the second aspect into a cell to be examined and a second harmonic detection step of detecting a second harmonic released from the compound for generating a second harmonic of light introduced into the cell.

Effects of the Invention

According to the present invention, a dye that effectively acts on a cell membrane, and generates a SHG signal but has suppressed generation of a TPF signal can be applied to SHG imaging, and observation of a cell membrane can be thus carried out with minimized damage to living tissues.

PREFERRED MODE FOR CARRYING OUT THE INVENTION

Hereinbelow, embodiments of the present invention will be more specifically described, but the present invention is not limited to the following embodiments and can be carried out by appropriately making a change within the range of the objects of the invention. Note that there may be a case when the explanation of a part is suitably omitted where the explanation is repeated, which however does not restrict the essence of the present invention.

The first aspect of the present invention is a compound for generating a second harmonic of light, which is an azobenzene derivative expressed by the formula (1) or a salt thereof:

(1)

(wherein each of R1 and R2 independently represents a straight-chain or branched alkyl group having 6 to 12 carbon atoms, and each of R3 to R18 independently represents a substituent selected from hydrogen, halogen, an alkyl group, an alkoxy group, an aryl group, an amino group, a hydroxyl group, a nitro group and a cyano group, R5 and R6, R9 and R10, R13 and R14, and R17 and R18 may combine together and form a ring structure having 5 to 7 carbon atoms. X represents —N+R19R20R21, a sulfonyl group, a carboxyl group, or an —OR group. Here, each of R19, R20 and R21 independently represents a straight-chain or branched alkyl group having 1 to 5 carbon atoms, and —OR represents a monovalent polyalkylene oxide group having an alkoxy group in the end. Provided that a is 0 or 1, b is 0 or 1, and n is an integer from 1 to 10.)

A compound for generating a second harmonic of light, which is an azobenzene derivative expressed by the formula (1) or a salt thereof, is introduced into a cell, thereby enabling the measurement and visualization of membrane electrical potential using SHG which is excellent in terms of time resolution ability and quantitativity.

Each of R1 and R2 in the formula (1) independently represents a straight-chain or branched alkyl group having 6 to 12 carbon atoms, and is a hydrophobic moiety for the interaction of the compound of the first aspect of the present invention with a cell membrane. The number of carbon atoms is preferably from 6 to 12, and more preferably from 6 to 10. SHG is generated when two photons interact with a non-centrosymmetric substance, and SHG is substantially allowed to be generated only in a compound present in the surface or interface of a cell membrane with broken spatial inversion symmetry. Herein, when the number of carbon atoms in R1 and R2 is 6 or more, interaction with a cell membrane is high, and when introduced into a cell, the R1 and R2 portion is inserted into a cell membrane so that the compound has a non-centrosymmetric distribution. As a result, the introduced compound is allowed to express SHG activity. The number of carbon atoms in R1 and R2 of 12 or less is preferable since hydrophilicity of the compound is not extremely damaged.

X in the formula (1) represents —N+R19R20R21, a sulfonyl group, a carboxyl group or an —OR group and is a hydrophilic moiety for retaining water solubility of the compound of the first aspect of the invention. Herein, each of R19, R20 and R21 independently represents a straight-chain or branched alkyl group having 1 to 5 carbon atoms, and —OR represents monovalent polyalkylene oxide having an alkoxy group in the end. In particular, it is preferable to select —N+R19R20R21, a sulfonyl group or a carboxyl group for improvement of solubility into water or a hydrophilic solvent.

In the compound of the first aspect of the present invention, when X in the formula (1) is —N+R19R20R21 and a=b=0 is satisfied, it is preferable from the viewpoint of balance between hydrophilicity and hydrophobicity of the compound. n is preferably from 1 to 10, and more preferably from 3 to 8. 1 or more of n is preferable since there is no problem of toxicity and an adverse effect on a cell is small, and 10 or less of n is preferable since there is no problem of solubility.

The compound of the first aspect of the present invention has a specific characteristic, such as showing SHG activity but not showing TPF activity by optimizing a structural part interposed between "—NR1R2" and "—(CH2)n-X" in the structure of the formula (1).

A compound used for SHG imaging is required to have interaction with two photons and a high efficiency of generating a second harmonic of light as its result. Irradiation of more intensive incident light is required in order to obtain a stronger signal; however, when irritated with an excessively intensive laser light, for example, the possibility of causing optical damage to a living tissue or the optical degradation of a dye itself is increased, thus being not desirable. Accordingly, the compound is required to effectively interact with two photons to generate SHG in order to obtain intensive SHG light with as weak an exciting light intensity as possible. In general, as a method of improving nonlinear optical characteristics in organic compound materials, a method of selecting an appropriate electron donating and absorbing substituent to enlarge a conjugated system is employed. In the compound of the first aspect of the present invention, for example, a or b is 1 to extend the resonance structure, and R5 and R6, R9 and R10, R13 and R14, and R17 and R18 are formed into a ring structure to be a quinoline or naphthalene structure, which thus makes it possible to adjust the conjugated system.

Examples of an alkyl group that can be represented by the above described R3 to R18 include alkyl groups having about 1 to 4 carbon atoms, such as a methyl, ethyl, propyl, isopropyl or butyl group. Examples of the alkoxy group include alkoxy groups having about 1 to 6 carbon atoms, such as a methoxy, ethoxy, isopropoxy, butoxy, isobutoxy, sec-butoxy, tert-butoxy or pentoxy group. Examples of the aryl group include aryl groups having about 6 to 14 carbon atoms, such as a phenyl group or a naphthyl group.

Among them, R5 and R6, R9 and R10, R13 and R14, and R17 and R18 may be combined together and form a ring structure having 5 to 7 carbon atoms. When these groups form a ring structure, a quinoline or naphthalene structure is preferably formed.

As a compound of the formula (1), compounds expressed by the structural formulas (2) and (3) described below are particularly preferable. Herein, the contents indicated by symbols such as R1 to R18, X, and n are the same as defined in the formula (1). In addition, each of R22 to R29 independently represents hydrogen or an alkyl group.

Examples of an alkyl group that can be represented by the above described R22 to R29 include alkyl groups having about 1 to 4 carbon atoms such as a methyl, ethyl, propyl, isopropyl or butyl group.

A specific example of the compound of the first aspect of the present invention includes a compound expressed by the structural formula described below.

-continued

An azobenzene derivative expressed by the formula (1) may exist in the form of a salt in certain cases. The kind of the salt of the present invention is not particularly limited, and examples thereof include inorganic acid salts such as a ClO4- addition salt, hydrochloride, sulfate, nitrite and phosphate, and organic acid salts such as acetate, maleate, fumarate and citrate.

The second aspect of the present invention is a dye composition for generating a second harmonic of light containing the compound of the above described first aspect. The form of the dye composition of the present invention is not particularly limited and may take any form, such as a solution, a suspension, or powder as long as it contains the compound of the first aspect. In particular, the form of a solution is preferable from the viewpoint of easiness of handling.

An azobenzene derivative expressed by the formula (1) or a salt thereof can be prepared into a solution of a dye composition for generating a second harmonic of light by dissolving into a suitable solvent (for example, water, lower alcohols such as methanol, and a non-protonic polar solvent, such as dimethyl sulfoxide). The azobenzene derivative or a salt thereof may further contain a compound that is usually added to a compound used in observation of a cell or a cell membrane by a fluorescent dye, such as a suitable buffer or preservative. It is also possible to add a physiologically active substance that induces membrane electrical potential activity by activating a cell when stimulation, such as a light, is received.

The third aspect of the present invention is a cell examination method utilizing a second harmonic that is generated by the compound for generating a second harmonic of light of the first aspect around a cell membrane, and including a dye introduction step of introducing the dye composition for generating a second harmonic of light of the second aspect into a cell to be examined and a second harmonic detection step of detecting a second harmonic that is released from the compound for generating a second harmonic of light introduced into the cell.

In the dye introduction step in the third aspect of the present invention, in order to introduce a dye composition for generating a second harmonic of light into a cell to be observed, a method used in observation by a fluorescent dye can be used without particular restriction.

For example, a cell that is extracted from a living body is immersed into a solution of the composition of the second aspect containing the compound for generating a second harmonic of light of the first aspect of the present invention at an appropriate concentration for a predetermined time and the compound for generating a second harmonic of light of the first aspect of the present invention can be thus applied to the cell. In addition, the solution of the composition of the second aspect may be supplied to the cell by a pipette.

In the second harmonic detection step in the third aspect of the present invention, a two-photon laser scanning microscope can be preferably used. Herein, the two-photon laser scanning microscope means a microscope that focuses a near-infrared pulse laser on a sample to be scanned and detects the SHG signal generated by the two-photon phenomenon on the sample to obtain an image.

As long as a two-photon laser scanning microscope that can be used has a laser light source generating a monochromatic coherent light pulse for a subpicosecond at a wavelength in the near-infrared range, a luminous flux conversion optical system for converting a luminous flux from the laser light source to a desired intensity, a scanning optical system for collecting the luminous flux converted in the luminous flux conversion optical system onto an image surface of an objective lens and having a light scan, an objective lens system for projecting the above described collected converted luminous flux onto the specimen surface, and a light detector, it can be used without particular limitation.

Pulse laser light is collected by the luminous flux conversion optical system and the objective lens system through a dichroic mirror to conjugate a focus on the specimen surface, thereby allowing the compound for generating a second harmonic of light present in the specimen to generate SHG induced by two-photon interaction. The specimen surface is scanned with a laser beam to detect a fluorescent intensity at each position by a light detecting apparatus, such as a light detector and the fluorescent intensity is plotted by a computer based on the obtained position information to thus obtain a two-dimensional or three-dimensional image. As a scanning mechanism, for example, scanning may be conducted by a laser beam using a mobile mirror such as a galvanometer mirror, or a specimen containing an optical second harmonic generation material placed on a stage may be moved.

A two-photon excitation laser scanning microscope can attain a high spatial resolution ability both in the in-plane and high axial directions utilizing the nonlinear effect of absorption of two photons itself due to such a structure.

The compound of the first aspect of the present invention has a membrane electrical potential sensitivity in a cell membrane since a part of the compound is buried into the cell membrane. Therefore, a light intensity of an SHG signal light generated by the compound varies depending on a change in electrical potential of a cell membrane.

In the cell examination method according to the present embodiment, a change in a light intensity of an SHG signal light caused by a membrane electrical potential sensitivity is used as a method for the optical measurement of electrical potential, which thus makes it possible to measure a signal intensity by several times to several tens of times as compared to a conventional technique. Furthermore, with a high special resolution ability of a two-photon excitation laser scanning microscope, a change over time of electrical potential in a cell membrane can be indirectly observed as a change over time of a SHG signal light. For example, information processing in a nerve cell is conducted as a change in electrical potential in a cell membrane and, therefore, the cell examination method according to the present embodiment is particularly effective for observing information processing in a nerve cell.

Since development of the patch clamp technique, an electrophysiological technique has been mainly employed for the measurement of electrical potential in a nerve cell membrane. However, a nerve cell has a very complicated structure, and many of the spines that are considered to be crucial for information processing and the dendrites that support the spines have very fine structures with a diameter of less than 1 micron. Therefore, the size of a glass electrode becomes a problem and the application of such an electrophysiological technique to a very fine structure had limitations. In the cell examination method according to the present embodiment, the second harmonic detection step does not depend on a cell form and the cell examination method is thus particularly useful for observing information processing in a nerve cell using a subject having a fine structure. In addition, a conventional membrane electrical potential measurement by patch clamp is simultaneously carried out, thereby making it possible to obtain more information.

When such observation of information processing in a nerve cell is conducted, it is useful to provide a cell stimulation step inducing a change in electrical potential in a cell membrane after the dye introduction step of introducing a dye into a nerve cell and before the second harmonic detection step. For inducing a change in electrical potential in a cell membrane, methods generally employed can be adopted without particular limitation, and examples thereof include electric stimulation by an inserted electrode, such as a patch clamp, and introducing a physiologically active substance which induces membrane electrical potential activity by activating a cell when light is received into the cell, and irradiating any stimulation region with a stimulating light (UV laser light) to give excitatory stimulation to the cell in the stimulation region.

For example, caged glutamate obtained by attaching a side chain (caged compound) that inactivates a physiological activity of glutamic acid to glutamic acid being a physiologically active substance is used as the above described physiologically active substance which induces membrane electrical potential activity by activating a cell when light is received. The caged glutamate is usually inactive, but when irradiated with ultraviolet light, its compound cleaves and glutamic acid is dissociated to induce a physiological activity. In addition, in place of caged glutamate obtained by combining glutamic acid with a caged compound, for example, a caged reagent obtained by combining amino acid, cyclic nucleotide (cNMPs) or calcium, which induces a physiological activity, with a caged compound, or photosensitivity channel molecules, such as channelrhodopsin, may be also used.

The cell examination method according to the present embodiment enables clarification of a physiological change in a wide space-time region from a fine structure of each cell, such as a nerve and a blood vessel, to the entire tissue, and is useful for pathophysiologic clarification of brain functional disorder, and the like.

EXAMPLES

Hereinbelow, the present invention will be more specifically described in view of examples, but the invention is not limited to the examples.

Synthesis Example 1

Synthesis of Ap1

First Step 15.0 ml (94.0 mmol) of an aqueous 42% tetrafluoroboric acid solution and 0.478 g (5.08 mmol) of 4-aminopyridine was added to a 100 ml recovery flask and the mixture was stirred and cooled with ice. 0.357 g (5.17 mmol) of sodium nitrite was gradually added to this, and 1.21 g (9.99 mmol) of N,N-dimethylaniline was also gradually dropped into it, and the reaction mixture was stirred at room temperature for 16 hours. An aqueous sodium hydroxide solution was added to adjust the pH to about 12, an orange crystal was deposited and suction filtration was then carried out to obtain a crystal. The crystal was dissolved into chloroform and filtered. The filtrate was collected into a 100 ml recovery flask, and the solvent was distilled off by an evaporator to thus obtain a crude crystal. This crude crystal was recrystallized with toluene:hexane to thus obtain 0.441 g (1.95 mmol) of an orange crystal compound 1 (yield: 38%). The spectral data of the obtained crystal compound 1 is shown in the following.

1H-NMR (CDCl3 270 MHz) δ: 3.13 (s, 6H), 6.76 (dd, J1=2.2 Hz, J2=8.1 Hz, 2H), 7.63 (dd, J1=1.5 Hz, J2=5 0.4 Hz, 2H), 7.91 (dd, J1=2.2 Hz, J2=8.1 Hz, 2H), 8.71 (dd, J1=1.5 Hz, J2=5.4 Hz, 2H)

Second Step 49.6 mg (0.219 mmol) of the compound 1, 46.6 mg (0.154 mmol) of 3-bromopropyltriethyl ammonium bromide and 1.22 ml of acetonitrile was added to a pressure-proof tube, and the mixture was bubbled with N2 for 5 minutes and stirred with heating at 80° C. for 23 hours. The reaction solution was transferred into a 50 ml recovery flask and the solvent was distilled off. Decantation was carried out with ethyl acetate and acetone, respectively. The reaction solution was dissolved into 100 ml of distilled water and transferred into a separating funnel, and operations of washing with 100 ml of ethyl acetate were carried out three times. Water was distilled off with an evaporator to thus obtain 37.5 mg (70.9 mmol) of Ap1 being a purple solid (yield: 46%). The spectral data of the obtained Ap1 is shown in the following.

1H-NMR (CDCl3 270 MHz) δ: 1.50 (t, J=7.2 Hz, 9H), 2.85-2.98 (m, 2H), 3.25 (s, 6H), 3.44 (q, J=7.2 Hz, 6H), 3.84 (t, J=8.0 Hz, 2H), 5.23 (t, J=7.8 Hz, 2H), 6.80 (d, J=9.4 Hz, 2H), 7.98 (d, J=9.4 Hz, 2H), 8.04 (d, J=7.0 Hz, 2H), 10.0 (d, J=7.0 Hz, 2H)

Synthesis Example 2

Synthesis of Ap2

First Step 1.72 g (18.5 mmol) of aniline, 50 ml of anhydrous DMF, 3.43 g (32.4 mmol) of sodium carbonate, and 7.00 ml (59.8 mmol) of 1-iodobutane was added to a two-necked flask and replaced with nitrogen. The reaction mixture was refluxed at 95° C. and stirred with heating for 20 hours, and then left to cool to room temperature. 100 ml of water was added to this and the reaction mixture was transferred into a separating funnel and extracted with 100 ml of ethyl acetate twice. The ethyl acetate layer was washed with 50 ml of water twice and washed with 50 ml of saturated saline once, and the solvent was distilled off. The reaction solution was purified by silica gel column chromatography (DCM:hex=1:9, v/v) to thus obtain 3.09 g (15.0 mmol) of a transparent oily liquid (yield: 81%). The spectral data of the obtained oily liquid is shown in the following.

1H-NMR (CDCl3 270 MHz) δ: 0.95 (t, J=7.3 Hz, 6H), 1.35 (tq, J1=7.3 Hz, J2=7.6 Hz, 4H), 1.56 (tt, J1=7. 6 Hz, J2=7.7 Hz, 4H), 3.25 (t, J=7.7 Hz, 4H), 6.59 (d, J=7.2 Hz, 1H), 6.63 (d, J=8.1 Hz, 2H), 7.19 (dd, J1=7.2 Hz, J2=8.1 Hz, 2H)

Second Step 14.6 ml (91.5 mmol) of an aqueous 42% tetrafluoroboric acid solution and 0.235 g (2.49 mmol) of 4-aminopyridine was added to a 100 ml recovery flask and the mixture was stirred and cooled with ice. 1.01 g (4.93 mmol) of N,N-dibutylaniline, 11.0 ml of ethanol, and 11.0 ml (68.9 mmol) of 42% tetrafluoroboric acid was added to a 30 ml conical flask, and the mixture was stirred and cooled with ice. 0.171 g (2.48 mmol) of sodium nitrite was gradually added to the solution in the 100 ml recovery flask that was stirred and cooled with ice. The solution in the 30 ml conical flask that was stirred and cooled with ice was gradually dropped into this, and the reaction solution was then stirred at room temperature for 15 hours. An aqueous sodium hydroxide solution was added to the reaction solution to adjust the pH to about 12, and 25 ml of saturated saline was added thereto, and the solution was then transferred into a separating funnel and extracted with 150 ml of ethyl acetate twice. The ethyl acetate layer was washed with 300 ml of saturated saline and dried with anhydrous sodium sulfate, and the solvent was then distilled off by an evaporator. The reaction solution was further purified by silica gel column chromatography (EA:hex=1:3, v/v) to thus obtain 0.185 g (0.589 mmol) of a compound 2 being a reddish-brown viscous solid (yield: 24%). The spectral data of the obtained compound 2 is shown in the following.

1H-NMR (CDCl3 270 MHz) δ: 0.99 (t, J=7.3 Hz, 6H), 1.40 (tq, J1=7.3 Hz, J2=15 Hz, 4H), 1.61-1.70 (m, 4H), 3.38 (tt, J=7.7 Hz, 4H), 6.69 (dd, J1=2.1 Hz, J2=7.2 Hz, 2H), 7.62 (dd, J1=1 0.6 Hz, J2=4.7 Hz, 2H), 7.87 (dd, J1=2.1 Hz, J2=7.2 Hz, 2H), 8.70 (dd, J1=1.6 Hz, J2=4.7 Hz, 2H)

Third Step

48.9 mg (0.158 mmol) of the compound 2, 51.4 mg (0.170 mmol) of 3-bromopropyltriethyl ammonium bromide, and 0.80 ml of acetonitrile was added to a pressure-proof tube, and the mixture was bubbled with N2 for 5 minutes and stirred with heating at 100° C. for 24 hours. The reaction solution was transferred into a 50 ml recovery flask, the solvent was distilled off, and decantation was then carried out with toluene. 96.1 mg (0.157 mmol) of Ap2 being a purple solid (yield: 99%) was obtained. The spectral data of the obtained Ap2 is shown in the following.

1H-NMR (CDCl3 270 MHz) δ: 1.01 (t, J=7.3 Hz, 6H), 1.36-1.51 (m, 17H), 2.80-2.97 (m, 2H), 3.41-3.80 (m, 10H), 3.83 (t, J=7.7 Hz, 2H), 5.18 (t, J=7.9 Hz, 2H), 6.75 (d, J1=9.3 Hz, 2H), 7.94 (d, J=9.3 Hz, 2H), 8.01 (d, J=6.7 Hz, 2H), 9.87 (d, J=6.7 Hz, 2H)

Synthesis Example 3

Synthesis of Ap3

First Step 2.30 ml (14.4 mmol) of an aqueous 42% tetrafluoroboric acid solution and 38.4 mg (0.408 mmol) of 4-aminopyridine was added to a 30 ml recovery flask and the mixture was stirred and cooled with ice. 0.208 g (0.794 mmol) of N,N-dihexylaniline, 1.70 ml of ethanol, and 1.70 ml (10.7 mmol) of 42% tetrafluoroboric acid was added to a 10 ml conical flask, and the mixture was stirred and cooled with ice. 30.3 mg (0.439 mmol) of sodium nitrite was gradually added to the solution in the 30 ml recovery flask that was stirred and cooled with ice. The solution in the 10 ml conical flask that was stirred and cooled with ice was gradually dropped into this, and the reaction mixture was then stirred at room temperature for 19 hours. An aqueous sodium hydroxide solution was added to the mixture to adjust the pH to about 12, and 5 ml of saturated saline was added to this, and the reaction solution was then transferred into a separating funnel and extracted with 25 ml of ethyl acetate twice. The ethyl acetate layer was washed with 80 ml of saturated saline and dried with anhydrous sodium sulfate, and the solvent was then distilled off by an evaporator. The reaction solution was further purified by silica gel column chromatography (EA:hex=1:3, v/v) to thus obtain 22.3 mg (0.0608 mmol) of a compound 3 [(E)-N,N-dihexyl-4-(pyridin-4-yldiazenyl)aniline] which is a reddish-brown viscous solid (yield: 15%). The spectral data of the obtained compound 3 is shown in the following.

1H-NMR (CDCl3 270 MHz) δ: 0.91 (t, J=6.7 Hz, 6H), 1.28-1.43 (m, 12H), 1.55-1.71 (m, 4H), 3.37 (t, J=7.7 Hz, 4H), 6.68 (dd, J1=1.9 Hz, J2=6.3 Hz, 2H), 7.62 (dd, J1=1.6 Hz, J2=4.6 Hz, 2H), 7.87 (dd, J1=1.9 Hz, J2=6.3 Hz, 2H), 8.70 (dd, J1=1.6 Hz, J2=4.6 Hz, 2H)

Second Step 51.8 mg (0.141 mmol) of the compound 3, 29.7 mg (98.0 μmol) of 3-bromopropyltriethyl ammonium bromide, and 1.22 ml of acetonitrile was added to a pressure-proof tube, and the mixture was bubbled with N2 for 5 minutes and stirred with heating at 80° C. for 23 hours. The reaction solution was transferred into a 50 ml recovery flask, the solvent was distilled off, and decantation was then carried out with ethyl acetate. The resultant product was dissolved into 100 ml of distilled water and transferred into an extraction funnel, and washing with 100 ml of ethyl acetate was carried out 8 times. Water was distilled off by an evaporator to thus obtain 51.6 mg (77.1 μmol) of Ap3 being a purple solid (yield: 79%). The spectral data of the obtained Ap3 is shown in the following.

1H-NMR (CDCl3 270 MHz) δ: 0.92 (t, J=6.62 Hz, 6H), 1.42-1.25 (m, 12H), 1.50 (t, J=7.0 Hz, 9H), 1.60-1.77 (m, 8H), 2.83-2.98 (m, 2H), 3.45 (q, J=7.2 Hz, 6H), 3.83 (t, J=8.0 Hz, 2H), 5.20 (t, J1=7.8 Hz, 2H), 6.74 (d, J=9.4 Hz, 2H), 7.94 (d, J=9.4 Hz, 2H), 8.00 (d, J=6.8 Hz, 2H), 9.90 (d, J=6.8 Hz, 2H)

SHG imaging was carried out in accordance with the following procedure using the above described Ap1 to Ap3 and a commercially available SHG imaging dye, FM4-64. FM4-64 is a compound having the structure described below.

FM4-64

Comparative Example 1

A buffer containing 100 μM of FM4-64 was prepared and introduced into a cultured human normal astrocyte using a pipette. The dye that was introduced into the cell spreads throughout the entire cell over time.

Figure 1:
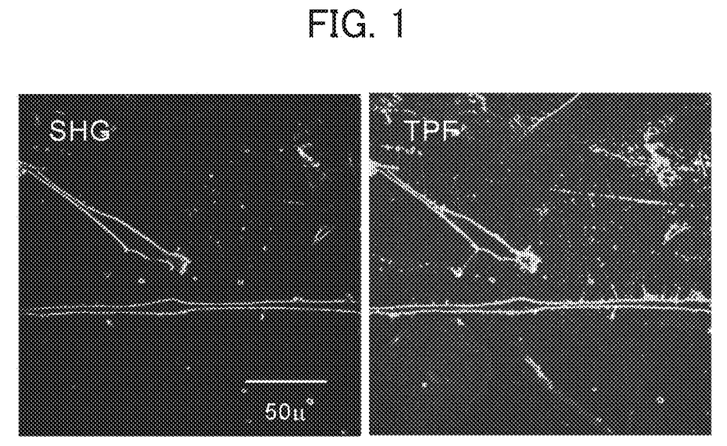
FIG. 1 illustrates a view showing SHG and TPF signals in Comparative Example 1.

For the measurement, a multiphoton microscope capable of SHG imaging and TPF imaging obtained by incorporating a tunable femtosecond mode synchronous infrared laser into a commercially available confocal laser scanning microscope was used as the light source. By irradiating with 1,000 nm of exciting light, an SHG signal light having a wavelength of 500 nm is generated from the dye in the same direction as the direction in which an infrared pulse laser travels. The signal can be detected in a photomultiplier tube provided on the laser light traveling direction side. A back scattered component of the TPF signal light is also observed by irradiating with the same exciting light. FIG. 1 shows the obtained SHG and TPF images.

Comparative Examples 2, 3 and Example 1

Figure 2:
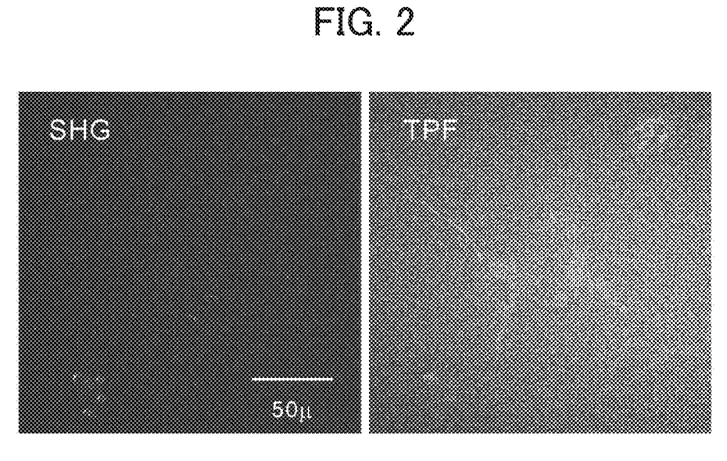
FIG. 2 illustrates a view showing SHG and TPF signals in Comparative Example 3.
Figure 3:
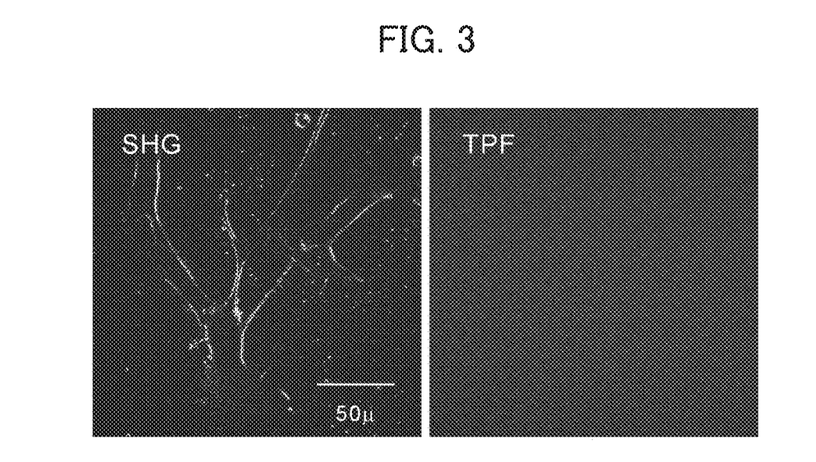
FIG. 3 illustrates a view showing SHG and TPF signals in Example 1.

SHG and TPF imaging was carried out in the same manner as Comparative Example 1 except for using Ap1 to Ap3 as dyes, and these cases were Comparative Examples 2 and 3 and Example 1, respectively. FIG. 2 shows an image obtained in Comparative Example 3 (the case of using Ap2), and FIG. 3 shows an image obtained in Example 1 (the case of using Ap3). Herein, an image of Comparative Example 2 using Ap1 is not described since an SHG signal light could not be observed.

A TPF signal is also observed except for an SHG signal in the example using FM4-64 in FIG. 1. On the contrary, an SHG signal is hardly observed in FIG. 2 using Ap2. A TPF signal was also very weak.

On the other hand, in the case of using Ap3 that is the dye for generating a second harmonic of light of the present invention, while an SHG signal can be observed as apparent from FIG. 3, a TPF signal was not observed.

Furthermore, using anionic, neutral, zwitter, and dicationic dyes shown in Table 1, solubility into a buffer, toxicity, and presence or absence of SHG and TPF signals when applied to cultured cells (CHO cells) were evaluated, respectively. Herein, the dyes #1 to 5 are dyes for generating a second harmonic of light outside of the range of the present invention, and the dyes #6 and 7 are dyes for generating a second harmonic of light within the range of the present invention.

TABLE 1

| Symbols | Properties | Chemical structures | The number of carbon atoms in R1 and R2 | Remarks |
|---|---|---|---|---|
| #1 | Anionic | | 4 | Outside of the invention |
| #2 | Anionic | | 6 | Outside of the invention |
| #3 | Anionic | | 8 | Outside of the invention |
| #4 | Neutral | | 6 | Outside of the invention |
| #5 | Neutral | | 6 | Outside of the invention |
| #6 | Zwitterionic | | 6 | Within the invention |
| #7 | Zwitterionic | | 8 | Within the invention |
| ap3 | Dicationic | | 6 | Within the invention |

Among the dyes for generating a second harmonic of light described above in Table 1, synthesis methods of the zwitterionic dyes #6 and 7 will be described in the following.

Synthesis Example 4

Synthesis of dye #6 [(E)-3-(4-((4-(dihexylamino)phenyl)diazenyl)pyridin-1-ium-1-yl)propane-1-sulfonate]

A solution obtained by dissolving 122 mg (1.0 mmol) of 1,3-propanesultone and 50 mg (0.14 mmol) of the compound 3 [(E)-N,N-dihexyl-4-(pyridin-4-yldiazenyl)aniline] which was synthesized in the first step of Synthesis Example 3 described above into dichloromethane (2 mL) was stirred at room temperature for 24 hours. After completion of the reaction, the solvent was distilled off and the residue was purified by silica gel column chromatography (solvent: dichloromethane/methanol=5/1) to thus obtain 32 mg (0.06 mmol) of the dye #6 (yield: 45%). Analytical results of the obtained compound by 1H-NMR and HRMS (high resolution mass spectrometry) are shown in the following.

1H-NMR (DMSO-d6, 400 MHz) δ: 0.88 (t, J=7.0 Hz, 6H), 1.31 (bs, 12H), 1.60 (bs, 4H), 2.22 (m, 2H), 2.46 (t, J=7.0 Hz, 2H), 3.52 (t, J=7.1 Hz, 4H), 4.66 (t, J=7.0 Hz, 2H), 6.95 (d, J=4.7 Hz, 2H), 7.91 (d, J=4.7 Hz, 2H), 8.10 (d, J=3.5 Hz, 2H), 8.97 (d, J=3.5 Hz, 2H)

HRMS(ESI): calculated value [C26H40N4O3S (M+Na)+]: 511.27133, observed value: 511.27059

Synthesis Example 5

Synthesis of dye #7 [(E)-3-(4-((4-(dioctylamino)phenyl)diazenyl)pyridin-1-ium-1-yl)propane-1-sulfonate]

First Step 2.1 g of 42% tetrafluoroboric acid was added to 201 mg (2.1 mmol) of 4-aminopyridine at 0° C. and stirred to obtain an emulsion. An aqueous solution obtained by dissolving 138 mg (2.0 mmol) of sodium nitrate into 5 mL of water was gradually added to this and the mixture was further stirred at 0° C. A mixture of 1.3 g (5.0 mmol) of N,N-dihexylaniline and acetic acid (3 mL) was added to this, and THF (5 mL) was further added to the reaction mixture, which was then stirred at room temperature for 3 hours. Then, an aqueous 2N sodium hydroxide solution (50 mL) was added and the mixture was extracted with ethyl acetate. The organic layer was dried with anhydrous sodium sulfate and then filtered, and the solvent as distilled off. The residue was purified by silica gel column chromatography (solvent: dichloromethane/methanol=15/1) to thus obtain 220 mg (0.6 mmol) of a target product (yield: 30%). Analytical results of the obtained compound 4 [(E)-N,N-dioctyl-4-(pyridin-4-yldiazenyl)aniline] by 1H-NMR are shown in the following.

1H-NMR (CDCl3, 400 MHz) δ: 0.89 (t, J=6.8 Hz, 6H), 1.29-1.34 (m, 20H), 1.64 (bs, 4H), 3.37 (t, J=7.7 Hz, 4H), 6.68 (d, J=4.5 Hz, 2H), 7.62 (d, J=3.0 Hz, 2H), 7.87 (d, J=4.5 Hz, 2H), 8.70 (d, J=3.0 Hz, 2H)

Second Step

A solution obtained by dissolving 122 mg (1.0 mmol) of 1,3-propanesultone and 42 mg (0.1 mmol) of the compound 4 into dichloromethane (2 mL) was stirred at room temperature for 24 hours. After completion of the reaction, the solvent was distilled off, and the residue was purified by silica gel column chromatography (solvent: dichloromethane/methanol=5/1) to thus obtain 42 mg (0.074 mmol) of the dye #7 (yield: 74%). Analytical results of the obtained compound by 1H-NMR and HRMS (high resolution mass spectrometry) are shown in the following.

1H-NMR (DMSO-d6,400 MHz) δ: 0.86 (t, J=7.0 Hz, 6H), 1.31 (m, 20H), 1.60 (bs, 4H), 2.24 (m, 2H), 2.46 (t, J=7.0 Hz, 2H), 3.52 (t, J=7.6 Hz, 4H), 4.66 (t, J=6.9 Hz, 2H), 6.95 (d, J=4.8H z, 2H), 7.91 (d, J=4.8 Hz, 2H), 8.10 (d, J=3.6 Hz, 2H), 8.96 (d, J=3.6 Hz, 2H)

HRMS(ESI): calculated value [C30H48N4O3S (M+Na)+]: 567.33393, observed value: 567.33375

Table 2 shows solubility and cytotoxicity of the dyes for generating a second harmonic of light #1 to 7 and Ap3 examined above and the presence or absence of SHG and TPF signals when applied to CHO cells. Herein, tests using the dyes #1 to 5 outside of the present invention were Comparative Examples 4 to 8, respectively. On the other hand, tests using the dyes #6, 7 and ap3 within the present invention were Examples 2 to 4, respectively.

[Evaluation of Solubility of Dyes]

DMSO (dimethyl sulfoxide) was added to the synthesized dye group (dyes #1 to #7) in Table 2 to have a concentration of a dye at about 100 mM and dissolving was attempted. The dyes #1, #2, and #3 were easily dissolved, on the other hand, poor solubility was observed in a part of the dyes #6 and #7, and no dissolving of the dyes #4 and #5 was observed.

[Evaluation of SHG and TPF Signals of Dyes]

DMSO solutions of the dyes #1 to #3, #4, #5 and Ap3 were diluted 1000 times using an extracellular fluid (Artificial Cerebrospinal Fluid), and when all were assumed to be dissolved, the final concentration was set at about 100 μM.

A CHO (Chinese Hamster Ovary) cell cultured on a cover glass was used as an observation subject, immersed into the above described dye solution to try dyeing a cell membrane, and directly observed under a microscope within several minutes.

Figure 4:
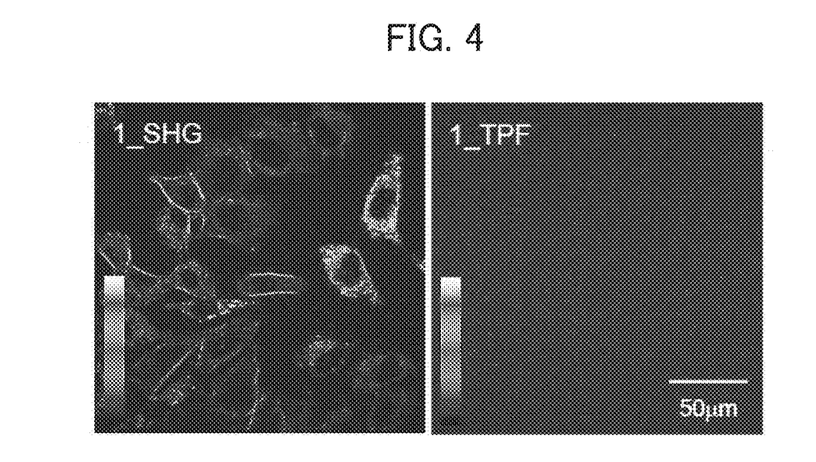
FIG. 4 illustrates a view showing SHG and TPF signals in Comparative Example 4.
Figure 5:
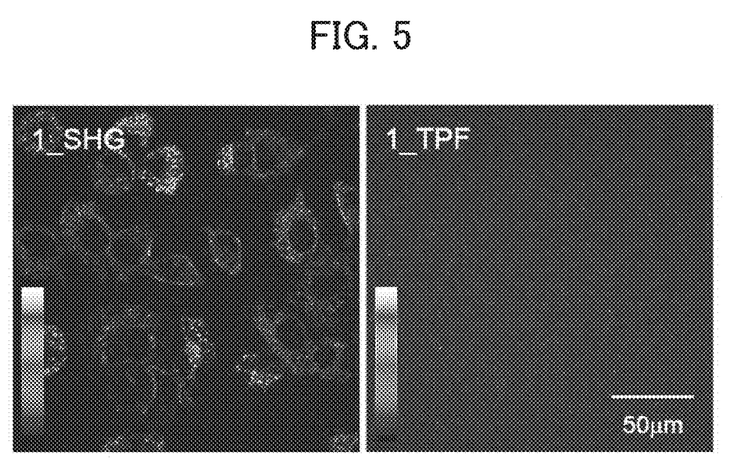
FIG. 5 illustrates a view showing SHG and TPF signals in Comparative Example 5.
Figure 6:
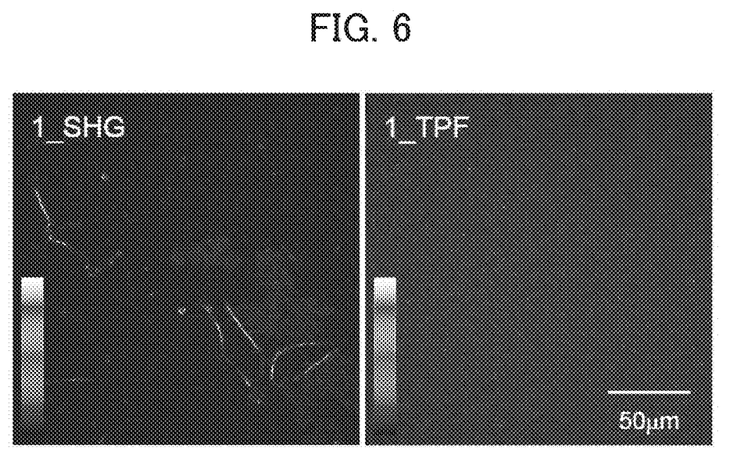
FIG. 6 illustrates a view showing SHG and TPF signals in Comparative Example 6.
Figure 7:
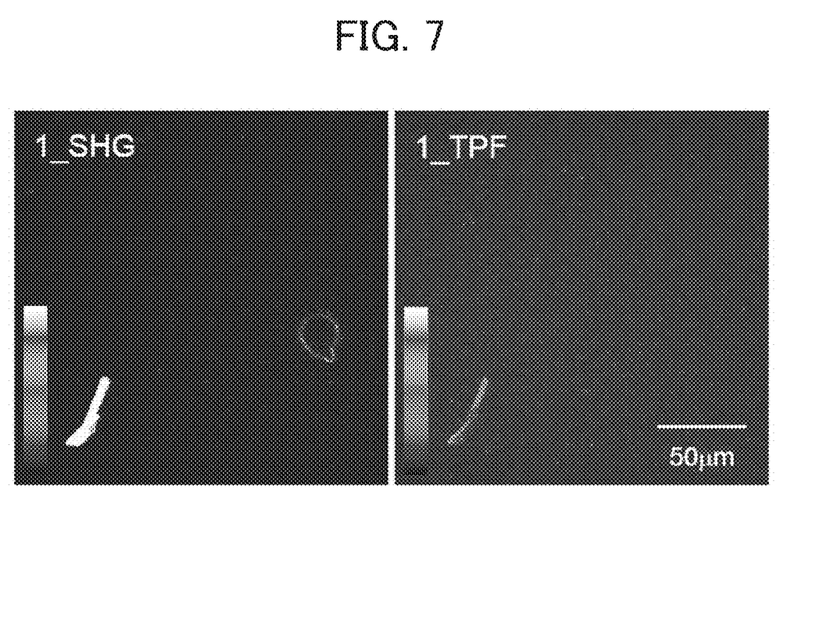
FIG. 7 illustrates a view showing SHG and TPF signals in Example 2.
Figure 8:
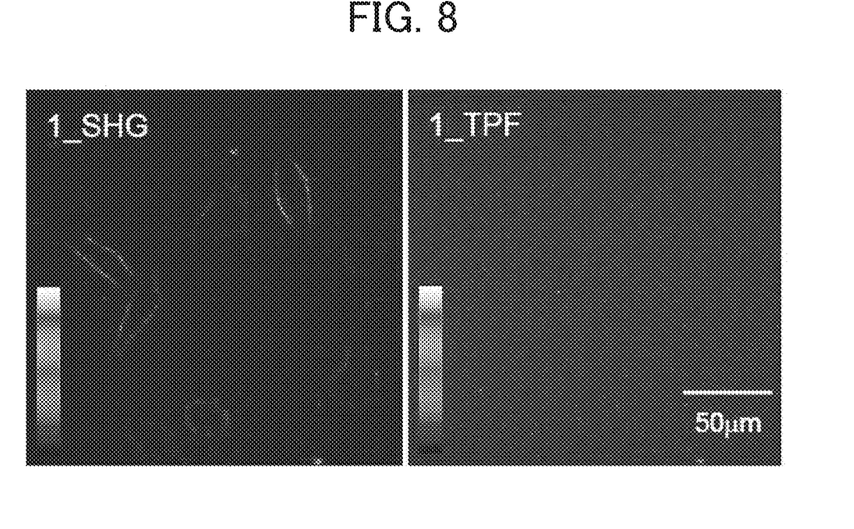
FIG. 8 illustrates a view showing SHG and TPF signals in Example 3.

A multiphoton laser microscope system (FV1000MPE manufactured by Olympus Corporation) on which an ultrashort femtosecond laser (MaitaiHP manufactured by Newport) was mounted was used for the observation, and SHG and two-photon fluorescence (Two-Photon Fluorescence: TPF) after irradiation by a pulse laser at 1,000 nm were observed under the same detection condition for each dye. Three images were obtained by changing fields of view per each dye, and signal intensities were qualitatively compared among the dyes. Among images obtained in the above described examination, one image per each dye is shown in FIGS. 4 to 8. FIGS. 4 to 6 show images of Comparative Examples 4 to 6, and FIGS. 7 and 8 show images of Examples 2 and 3, respectively.

In addition, both signals of SHG and TPF were not obtained at all from the dyes #4 and #5, which were incapable of dye dissolution and, therefore, the dyes cannot be evaluated (not applicable: n/a).

[Evaluation of Cytotoxicity of Dyes]

For evaluation of cytotoxicity due to a dye, cell forms before and after dyeing were confirmed from a differential interference figure using near-infrared light. Cytotoxicity was evaluated by particularly focusing on two points that 1) a cell having an extended structure due to interaction with an extracellular matrix loses its adhesion to thus separate from a cover glass and is rounded, and 2) a cell membrane having a smooth form becomes an inhomogeneous and uneven form, when the physiological condition of the cell deteriorates.

TABLE 2

| | Dyes used | Solubility (μM) | Toxicity | SHG signal | TPF signal |
|---|---|---|---|---|---|
| Comparative Example 4 | #1 | ~100 | High | Good | None |
| Comparative Example 5 | #2 | ~100 | High | Good | None |
| Comparative Example 6 | #3 | ~100 | Some | Good | None |
| Comparative Example 7 | #4 | Insoluble | n/a | n/a | n/a |
| Comparative Example 8 | #5 | Insoluble | n/a | n/a | n/a |
| Example 2 | #6 | <100 | Little | Fine | None |
| Example 3 | #7 | <100 | Little | Fine | None |
| Example 4 | ap3 | 100 | Little | Good | None |

Examples 2 to 4 using the dyes #6, 7 and ap3 within the present invention had no problem in solubility into a buffer and toxicity. When these dyes #6, 7 and ap3 were applied to a cell, a TPF signal was not observed, and only an SHG signal was observed. FIGS. 6 and 7 show SHG and TPF signals of Examples 2 and 3. From the above described examination, by introducing the dye of the present invention into a cell, it was confirmed that nonluminescent SHG imaging is possible and suggested that the measurement and visualization of membrane electrical potential are possible.

The invention claimed is:

1. A compound for generating a second harmonic of light, the compound being an azobenzene derivative of the following formula (1), or a salt thereof:

(wherein each of $R_1$ and $R_2$ independently represents a straight-chain or branched alkyl group having 6 to 12 carbon atoms, and each of $R_3$ to $R_{18}$ independently represents a substituent selected from hydrogen, halogen, an alkyl group, an alkoxy group, an aryl group, an amino group, a hydroxyl group, a nitro group and a cyano group, $R_5$ and $R_6$, $R_9$ and $R_{10}$, $R_{13}$ and $R_{14}$, and $R_{17}$ and $R_{18}$ may combine together and form a ring structure having 5 to 7 carbon atoms, X represents —$N^+R_{19}R_{20}R_{21}$, a sulfonyl group, a carboxyl group, or an —OR group, here, each of $R_{19}$, $R_{20}$ and $R_{21}$ independently represents a straight-chain or branched alkyl group having 1 to 5 carbon atoms, and —OR represents a monovalent polyalkylene oxide group having an alkoxy group in the end, provided that a is 0 or 1, b is 0 or 1, and n is an integer from 1 to 10).

2. The compound for generating a second harmonic of light according to claim 1, wherein X represents —$N^+R_{19}R_{20}R_{21}$ and a=b=0 is satisfied in the formula (1).

3. A dye composition for generating a second harmonic of light comprising at least the compound according to claim 1.

4. A cell examination method utilizing a second harmonic generated by a dye around a cell membrane, which comprises a dye introduction step of introducing the dye composition for generating a second harmonic of light according to claim 3 into a cell to be examined, and a second harmonic detection step of detecting a second harmonic released from the compound for generating a second harmonic of light introduced into the cell.

5. The cell examination method according to claim 4, comprising a cell stimulation step of inducing a change in membrane electrical potential in the cell membrane of the cell after the dye introduction step and before the second harmonic detection step.

6. The cell examination method according to claim 5, wherein a second harmonic is detected over time in the second harmonic detection step.

7. The cell examination method according to claim 4, wherein the cell is a nerve cell.

* * * * *